(12) United States Patent
Kuma et al.

(10) Patent No.: US 7,927,638 B2
(45) Date of Patent: *Apr. 19, 2011

(54) FERMENTED MILK DRINKS AND FOODS AND PROCESS FOR PRODUCING THE SAME

(75) Inventors: Yoshiharu Kuma, Tokyo (JP); Ryoichi Akahoshi, Tokyo (JP); Tatsuyuki Kudo, Tokyo (JP); Kojiro Kawami, Tokyo (JP); Miku Shibata, Kanagawa-ken (JP); Shinji Hashimoto, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 501 days.

This patent is subject to a terminal disclaimer.

(21) Appl. No.: 11/186,837

(22) Filed: Jul. 22, 2005

(65) Prior Publication Data

US 2005/0255193 A1 Nov. 17, 2005

Related U.S. Application Data

(62) Division of application No. 10/048,447, filed as application No. PCT/JP00/05095 on Aug. 1, 2000, now Pat. No. 7,115,291.

(30) Foreign Application Priority Data

Aug. 3, 1999 (JP) .................................... 11-220157
Jan. 14, 2000 (JP) ................................ 2000-005485

(51) Int. Cl.
   *A23C 9/12* (2006.01)
(52) U.S. Cl. ................ 426/43; 426/42; 426/36; 426/52; 426/61; 426/582; 426/583

(58) Field of Classification Search .................... 426/42, 426/43, 36, 52, 61, 582, 583
See application file for complete search history.

(56) References Cited

U.S. PATENT DOCUMENTS 3,891,773 A * 6/1975 Kline et al. ..................... 426/61
4,001,628 A   1/1977 Ryan
(Continued)

FOREIGN PATENT DOCUMENTS

CN     1270769 A     10/2000
(Continued)

OTHER PUBLICATIONS

Williams, W. L. et al. 1947. Oleic acid and related compounds as growth factors for lactic acid bacteria. J. Biol. Chem. 619-630.*

(Continued)

*Primary Examiner* — Keith D Hendricks
*Assistant Examiner* — Hamid R Badr
(74) *Attorney, Agent, or Firm* — Oblon, Spivak, McClelland, Maier & Neustadt, L.L.P.

(57) ABSTRACT

Fermented milk drinks and foods containing fermented milk components obtained by fermentation with lactic acid bacteria together with a growth promoter for lactic acid bacteria selected from among ginger extract, tea extract, green onion extract, or oleic acid and derivatives thereof, and a process for producing the fermented milk drinks and foods involving the step of culturing lactic acid bacteria in a medium containing the growth promoter for lactic acid bacteria. These fermented milk drinks and foods can contain a large number of viable cells of lactic acid bacteria and sustain the activity (acid producing ability) of the bacteria at a high level.

25 Claims, 2 Drawing Sheets

U.S. PATENT DOCUMENTS

| | | | |
|---|---|---|---|
| 4,298,620 A | 11/1981 | Hagiwara | |
| 4,656,044 A | 4/1987 | Sugimoto et al. | |
| 4,668,525 A | 5/1987 | Creswick | |
| 5,466,472 A | 11/1995 | Kuma et al. | |
| 5,820,901 A | 10/1998 | Nicolas et al. | |
| 5,827,560 A | 10/1998 | Fu et al. | |
| 5,879,733 A | 3/1999 | Ekanayake et al. | |
| 6,068,862 A | 5/2000 | Ishihara et al. | |
| 6,096,365 A | 8/2000 | Spisak et al. | |
| 6,165,536 A | 12/2000 | Heeb et al. | |
| 6,268,009 B1 | 7/2001 | Ekanayake et al. | |
| 6,299,925 B1 | 10/2001 | Xiong et al. | |
| 6,426,106 B1 | 7/2002 | Barrett et al. | |
| 6,713,109 B1 | 3/2004 | Lassota | |

FOREIGN PATENT DOCUMENTS

| | | | |
|---|---|---|---|
| DE | 198 53 178 | | 5/2000 |
| EP | 0 639 335 | | 2/1995 |
| EP | 0 649 603 | | 4/1995 |
| EP | 0 659 347 | | 6/1995 |
| GB | 1 197 257 | | 7/1970 |
| JP | 60-75233 | | 4/1985 |
| JP | 362257383 | * | 11/1987 |
| JP | 63-248344 | | 10/1988 |
| JP | 63248344 | * | 10/1988 |
| JP | 2-142497 | | 5/1990 |
| JP | 4-108334 | | 4/1992 |
| JP | 7-99968 | | 4/1995 |
| JP | 11-004 665 | | 1/1999 |
| KR | 1995-0011578 | | 10/1995 |
| KR | 0095469 | | 10/1995 |
| WO | WO 96/37113 | | 11/1996 |
| WO | WO 98/10666 | | 3/1998 |
| WO | 98/57555 | | 12/1998 |

OTHER PUBLICATIONS

Smittle, R. B. 1972. Death of *Lactobacillus bulgaricus* resulting from liquid nitrogen freezing. Appl. Microbiol. 24: 551-554.*
JP 03198743-A. Abstract.*
JP 06153853-A. Abstract.*
R. B. Smittle, et al., Applied Microbiology, vol. 24, No. 4, pp. 551-554, "Death of *Lactobacillus bulgaricus* Resulting From Liquid Nitrogen Freezing", Oct. 1972.
Patent Abstracts of Japan, JP 02-142497, May 31, 1990.
Patent Abstracts of Japan, JP 04-108334, Apr. 9, 1992.
Patent Abstracts of Japan, JP 60-075233, Apr. 27, 1985.
Database WPI, Section Ch, Week 199524, Derwent Publications Ltd., London, GB; AN 1995-182063, XP002299328 (1995).

* cited by examiner

FERMENTED MILK DRINKS AND FOODS AND PROCESS FOR PRODUCING THE SAME

TECHNICAL FIELD

This invention relates to fermented milks, each of which contains a fermented milk ingredient and a lactic acid bacteria growth factor selected from specific compounds, and also to processes for the production of the fermented milks.

BACKGROUND

Fermented milks, such as fermented milk drinks, lactic acid bacteria beverages, yoghurt, cultured milks and cheese, are often produced by providing animal milks, such as cow milk, goat milk, horse milk and the like, as culture media and fermenting them with lactic acid bacteria. However, such lactic acid bacteria generally have strict auxotrophy, and many strains thereof do not grow well in culture media composed solely of animal milks. Even with bacterial strains having relatively good proliferability, culture media composed of animal milks alone are considered to require continued cultivation over several days if fermented milk ingredients having acidity sufficient for use in the production of fermented milks are desired.

In the cultivation for the production of a fermented milk in which importance is placed on the viable cell count of lactic acid bacteria, long cultivation however gives rise to another problem in that it leads to a reduction in the viable cell count of the lactic acid bacteria. For example, fermented milks making use of fermented milk of the viable cell type, such as yoghurt, are extensively consumed as health-promoting foods having physiological effects such as intestinal function controlling effect and immunopotentiating effect. For the maintenance of these physiological effects at high levels, it is important to retain useful bacteria, such as lactic acid bacteria, in as high viable cell count as possible in a viable state and further to keep high the activity (acid producing ability). On the other hand, the flavor of a fermentation product is of importance for a fermented milk. This makes it impossible to choose a bacterial strain from the viewpoint of proliferability alone, and on the contrary, a bacterial strain may have to be selected for its ability to give fermentation products of good flavor despite its poor proliferability.

In the cultivation of lactic acid bacteria, it is therefore common practice to add one or more of various growth promoting substances to a culture medium in order to improve the efficiency of the cultivation. Currently known examples of growth promoting substances or those confirmed to be effective for the promotion of growth include *Chlorella* extract, iron salts, vitamins, proteolysates containing amino acids and peptides, and yeast extract. They are used for the above-mentioned purpose.

For the retention of the usefulness of lactic acid bacteria, it is necessary not only to promote its growth but also to inhibit death of its cells and further, is required to maintain a high viable cell count in the final product during storage. A marked reduction is observed in the viability of lactic acid bacteria especially when a low-fat fermented milk such as low-fat yoghurt is produced using skim milk powder or when lactic acid fermentation proceeds excessively. This problem becomes more serious when low-calorie fermented milks or low-pH fermented milks are produced. With a view to maintaining such viable cell counts, substances such as *Chlorella* are added these days.

The addition of such substances, however, often affects the flavors of products themselves and moreover, involves a problem in that the costs of the products are increased. In addition, these substances can hardly maintain the high activities of such lactic acid bacteria although they may be able to keep high viable cell counts.

An object of the present invention is therefore to find out a novel growth-promoting or viability-improving substance which is free of a problem with flavor and, when simply added, can increase the viable cell count of lactic acid bacteria and can also maintain the viable cell count in the final product, and further to provide a fermented milk which makes use of the substance to maintain as many cells of the lactic acid bacteria as possible in a viable state and also to keep high the activity (acid producing ability) of the cells.

DISCLOSURE OF THE INVENTION

The present inventors have proceeded with extensive screening for substances having the property of achieving growth promotion in and improving the viability of lactic acid bacteria. As a result, it has been found that extracts of ginger, tea and green onion as well as oleic acid and derivatives thereof have the above-mentioned property and also that their use in the preparation of fermented milks cause no problem with flavor, leading to the completion of the present invention.

The present invention therefore provides a fermented milk comprising a fermented milk ingredient obtained by lactic acid fermentation and a lactic acid bacteria growth factor selected from ginger extract, tea extract, green onion extract, or oleic acid or a derivative thereof.

The present invention also provides a process for the production of a fermented milk, which comprises culturing lactic acid bacteria in a culture medium in which one or more lactic acid bacteria growth factors selected from ginger extract, tea extract, green onion extract, and oleic acid and derivatives thereof is contained.

BEST MODES FOR CARRYING OUT THE INVENTION

Figure 1:
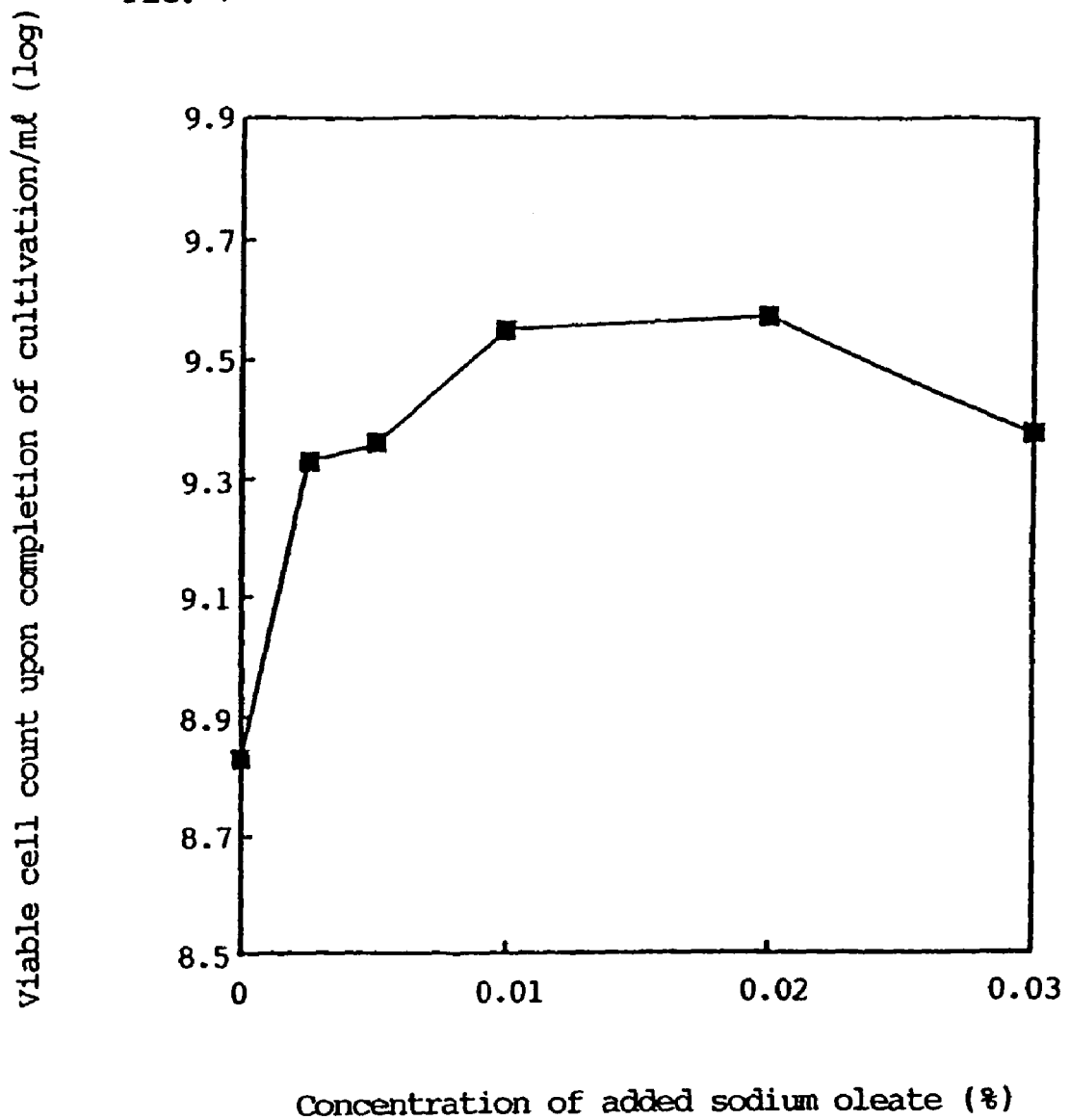
FIG. 1 is a plot of the relationship between concentration of added sodium oleate and viable cell count upon completion of cultivation of lactic acid bacteria.

The term "fermented milks" as used herein embraces drinks such as fermented milk and fermented drinks of lactic acid bacteria as specified in the Ordinance of the Ministry of Health and Welfare, the Government of Japan on Milk and Related Products; and hard yoghurt, soft yoghurt and plain yoghurt, and further kefir, cheese and the like.

On the other hand, the term "lactic acid bacteria growth factor" as used herein means a substance which can promote growth of lactic acid bacteria to increase its viable cell count upon cultivation and further can heighten the viability of the lactic acid bacteria to maintain its viable cell count subsequent to formation of a fermented milk, which has been obtained by the fermentation, into a final product.

The fermented milk according to the present invention is only required to contain a lactic acid bacteria growth factor, which is selected from ginger extract, tea extract or green onion extract, or oleic acid or a derivative thereof, in a fermented milk ingredient obtained by lactic acid fermentation. It is preferred to add the lactic acid bacteria growth factor before the lactic acid fermentation, although no limitation is imposed on the time of its addition. It can therefore be added in the course of the lactic acid fermentation or after completion of the lactic acid fermentation. Further, the lactic acid bacteria growth factor may be added in portions.

Among the lactic acid bacteria growth factors which can be added into the fermented milk ingredient in the present invention, the ginger extract means an extract obtained by extracting ginger, as it is or after subjecting it to processing such as peeling and/or crushing, in an organic solvent such as ethanol, ethyl acetate, glycerin or propylene glycol or a mixed solvent thereof. On the other hand, the tea extract means an extract of tea obtained by processing leaves of tea plant which is an evergreen shrub of genus *Camellia*, namely, an extract of non-fermented tea, half-fermented tea or fermented tea, specifically an extract obtained by extracting green tea, black tea, oolong tea, jasmine tea or the like in water or in an organic solvent such as ethanol, ethyl acetate, glycerin or propylene glycol or a mixed solvent thereof. Further, the green onion extract means an extract obtained by extracting green onion, as it is or after subjecting it to processing such as chopping or crushing, in water or in an organic solvent such as ethanol, ethyl acetate, glycerin or propylene glycol or a mixed solvent thereof. The green onion which is provided for the extraction may be either deep-planted green onion (Nebuka green onion)—only a white part of a leaf sheath of which, said white part being called "root" in general, is edible—or leaf green onion (Ha green onion) a green part of which is also edible.

Among the extracting solvents described above, water, especially a water-base acidic solvent is preferred. Use of a water-base acidic solvent is considered to result in extraction of a great deal of trace components (substances) which are contained in the extractive and are believed to have growth promoting effect for lactic acid bacteria. An extract available from the use of such a water-base acidic solvent, even when added in a small amount, can bring about excellent growth promoting effect, so that its influence to the flavor can be minimized.

As the solvent for the extraction and preparation of the ginger extract, the tea extract or the green onion extract, water-base solvents such as water and water-alcohol are preferred. It is particularly preferred to conduct the extraction by using a water-base solvent of a pH not higher than 4.0. No particular limitation is imposed on an acid for use in this acid extraction insofar as it is employed in foods. Illustrative of the acid are citric acid, malic acid, tartaric acid, succinic acid, lactic acid, and acetic acid. No particular limitation is imposed on conditions for the extraction, but it is preferred to extract at 60° C. or higher but 120° C. or lower, preferably at 80° C. or higher but 100° C. or lower for 30 to 60 minutes.

Of ginger extract, tea extracts and green onion extract available as described above, tea extracts are preferred for their high growth promoting effect on lactic acid bacteria, with oolong tea extract being particularly preferred. These extracts can be used either singly or in combination. When plural ones of the extracts are combined, they may be mixed together after they are obtained separately, or two or more of ginger, tea and green onion are mixed together, followed by extraction.

As these extracts, solutions immediately after extraction can be used as they are. As an alternative, they can also be used in the form of concentrated extracts obtained by a method such as ultrafiltration or centrifugation or in the form of powdery extracts obtained by drying such as spray drying or lyophilization.

No particular limitation is imposed on oleic acid or its derivative (hereinafter called "oleic acid or the like") out of the lactic acid bacteria growth factors usable in the present invention. Illustrative are, in addition to free oleic acid and inorganic salts of oleic acid, sucrose esters, glycerides, sorbitan esters propylene glycol esters and the like, which are widely used as emulsifiers and contain oleic acid as their fatty acid moieties. Specific examples can include sodium oleate, potassium oleate, glyceryl oleate, polyglyceryl oleate, sorbitan oleate, propylene glycol oleate, and sucrose oleate. Of these, monoglyceryl oleate and polyglyceryl monooleate are preferred as they are highly effective for increasing the viable cell count at the end of cultivation and also improving the viability of the cells. Sucrose oleate and the like are also preferred from the standpoint of physical properties such as solubility. These lactic acid bacteria growth factors can be used either singly or in combination.

Incidentally, a food material which contains a great deal of oleic acid or the like can also be used as a substitute for the growth factor. It is however to be noted that even among those containing oleic acid in their structures, those containing it in a form such as lysolecithin may not be able to bring about the advantageous effect of maintaining the count and activity of viable cells in the fermented milk according to the present invention.

The amount of the lactic acid bacteria growth factor, which is selected from ginger extract, tea extract or green onion extract or oleic acid or a derivative thereof, to be added to the fermented milk ingredient varies depending on the kind of the lactic acid bacteria growth factor to be used, the strain of lactic acid bacteria to be used, the kind of the culture medium to be used, the application purpose of the cultured product, and so on. It is therefore desired to empirically determine its amount.

In the case of ginger extract, tea extract or green onion extract (hereinafter called "the extract or the like")), for example, it is preferred to add it as an extract of 10% soluble solids (Brix 10°) in an amount of from about 0.02 wt. % to 2.0 wt. % (hereinafter simply referred to as "%"), notably from about 0.1% to 1.0% provided that the extract is obtained using hot water. An amount greater than 2.0% are not expected to bring about additional growth promoting effect and, when various drinks or foods are produced using the culture, may more or less affect their flavors. An amount smaller than 0.02%, on the other hand, leads to a some reduction in the growth promoting effect.

In the case of an extract obtained by acid extraction, it is preferred to add it as an extract of 10% soluble solids (Brix 10°) in an amount of from about 0.01% to 2.0%, notably from about 0.05% to 1.0% for similar reasons as mentioned above. An acid-extracted extract has high growth promoting effect, and can show excellent effect even when added in half the amount of the hot water extract.

Further, oleic acid or the like may preferably be added in an amount such that the final concentration after formation into a final product ranges from 15 µg/mL to 60 µg/mL, especially from 15 µg/mL to 40 µg/mL in terms of oleic acid. An amount smaller than 5 µg/mL leads to weak effect for the prevention of death of cells after formation into the final product, while an amount greater than 60 µg/mL gives rise to problems in that the product cost increases and the content of fat in the final product also increases, and further results in a reduced growth rate of cells.

On the other hand, the fermented milk ingredient obtained by lactic acid fermentation (hereinafter called "the fermented milk ingredient") can be obtained by fermenting an animal milk medium with lactic acid bacteria. As a material for the animal milk medium, it is possible to use fresh milk such as cow milk, goat milk or horse milk or a milk product such as skim milk powder, whole milk powder or fresh cream. To the medium, additives to ordinary culture media for lactic acid bacteria may also be added. Examples of such additives can include vitamins such as vitamin A, vitamin Bs, vitamin C and vitamin E, various peptides, various amino acids, and salts such as calcium and magnesium.

No particular limitation is imposed on the lactic acid bacteria for use in the fermentation. One or more lactic acid bacteria selected from *Lactobacillus* bacteria, *Streptococcus thermophilus* and *Lactococcus lactis* can be used in combination. Specific examples of lactic acid bacteria can include

*Lactobacillus casei, Lactobacillus acidophilus, Lactobacillus salivalius, Lactobacillus gallinarum, Lactobacillus gasseri, Lactobacillus fermentum, Lactobacillus helveticus, Lactobacillus jugulti, Lactobacillus delbrueckii* subsp. *bulgaricus, Streptococcus thermophilus, Lactococcus lactis* subsp. *lactis,* and *Lactococcus lactis* subsp. *cremoris.*

Use of oleic acid or a derivative thereof as a lactic acid bacteria growth factor is preferred owing to its high effect for the prevention of death, *Lactobacillus* species, *Lactococcus lactis* and *Streptococcus thermophilus.* When ginger extract, tea extract or green onion extract is used as a lactic acid bacteria growth factor, *Lactobacillus casei, Lactobacillus acidophilus, Lactobacillus gasseri, Lactococcus lactis* subsp. *lactis,* and *Lactococcus lactis* subsp. *cremoris* are preferred for a similar reason.

Whichever lactic acid bacteria growth factor is used, *Lactobacillus casei* is especially preferred. Further, cells commonly eaten, such as *Bifidobacterium* and yeast, may also be used in combination.

Oleic acid or the like, which is a growth factor for lactic acid bacteria in the present invention, shows particularly good effect when a low-fat fermented milk is prepared using skim milk powder, namely, liquid skim milk or powdery skim milk is used as a culture medium for the fermented milk ingredient of the fermented milk. Production of such a low-fat fermented milk can be conducted specifically by adding to a milk ingredient, which is composed of skim milk as a primary material, oleic acid or the like in an amount such that its final concentration after formation into a final product becomes 15 µg/mL or higher in terms of oleic acid and then fermenting the milk ingredient with lactic acid bacteria or by fermenting a milk ingredient, which is composed of skim milk as a primary material, with lactic acid bacteria and then adding oleic acid or the like in the above-described amount. Use of the former process is particularly preferred, because the viable cell count at the time of completion of cultivation is high and the viability of the cells is high. In these processes, the fermentation is practiced by inoculating the milk ingredient with the lactic acid bacteria and cultivating the bacteria at a temperature of about 35 to 37° C. for 3 to 5 days.

The combined use of one or more extracts selected from ginger extract, tea extract and green onion extract with oleic acid or the like in the present invention also makes it possible to synergistically achieve promotion of the growth of the lactic acid bacteria and an improvement in its viability. Excellent effect is available especially when tea extract and oleic acid or the like are used in combination, with combined use of oolong tea extract and oleic acid or the like being more preferred. When two or more of the lactic acid bacteria growth factors in the present invention are used in combination as described above, they can be added in similar amounts as described above.

Examples of the fermented milks of the present invention, which can be obtained as described above, can include drinks or foods making use of various lactic acid bacteria, for example, fermented milk drinks, lactic acid bacteria beverages, yoghurt, cultured milks, kefir, cheese and the like, illustrative types of which can be plain type, flavored type, fruit type, sweet type, soft type, drink type, hard type, frozen type and the like.

Upon production of the fermented milk, it is possible to use flavors such as yoghurt type, berry type, orange type, (Chinese) quince type, perilla type, citrus type, apple type, mint type, grape type, apricot type, pear, custard cream, peach, melon, banana, tropical, herb type, black tea, and coffee type; sugars such as sucrose, isomerized sugar, glucose, fructose, palatinose, trehalose, lactose, and xylose; sugar alcohols such as sorbitol, xylitol, erythritol, lactitol, paratinit, reducing thick malt syrup, and reducing thick maltose syrup; emulsifiers such as sucrose fatty acid esters, glycerin fatty acid esters, and lecithin; and thickeners (stabilizers) such as agar, gelatin, carageenan, guar gum, xanthan gum, pectin, and locust bean gum. It is also possible to add various vitamins such as vitamin A, vitamin Bs, vitamin C, and vitamin E; and minerals such as calcium, iron, and zinc.

The lactic acid bacteria growth factor selected from ginger extract, tea extract, green onion extract, or oleic acid or a derivative thereof has growth promoting effect or viability improving effect for lactic acid bacteria. Of these, ginger extract, tea extract and green onion extract are excellent especially in growth promoting effect for lactic acid bacteria. Oleic acid and its derivatives, on the other hand, have both growth promoting effect and viability improving effect for lactic acid bacteria, but their viability improving effect is greater.

INDUSTRIAL APPLICABILITY

The ginger extract, tea extract or green onion extract or oleic acid or the derivative thereof, which is added in the fermented milk according to the present invention has excellent growth promoting effect and viability improving effect for the lactic acid bacteria, and moreover, is free of a flavor which may pose a particular problem. Accordingly, the fermented milk with the growth factor has high utility as a drink or food which is excellent for the promotion of health and is free of a deterioration in flavor.

Especially in a low-fat fermented milk product making use of oleic acid or a derivative thereof as a lactic acid bacteria growth factor, death of cells is prevented even when cultivated from the stationary phase until the death phase, and further, excellent death preventing effect can be exhibited during refrigerated storage after formation into a final product and also for temperature rises during the storage. The lactic acid bacteria as many as about $1 \times 10^8$ cfu/mL are allowed to remain as viable cells. Even when the final product is stored at 10° C. for 2 weeks, a viability rate of 20% or higher can be maintained. When the cultivation of the low-fat fermented milk is allowed to proceed to the stationary phase or death phase of the lactic acid bacteria, use of *Lactobacillus casei, Lactococcus lactis Streptococcus thermophilus* or the like generally makes it possible to assure such viable cell count and viability rate of the lactic acid bacteria as mentioned above even when the pH of the final product drops to about 3.6 to 3.8, although the optimal pH and acid tolerance of cells vary depending on the bacterial strain and the cultivation time and the like hence vary depending on the cells. Further, use of skim milk for the provision of a fermented product and addition of oleic acid or a derivative thereof can limit the content of fat at 0.1 wt. % or so in the final product, so that the final product can be sold as a low-fat fermented milk of low calorie.

EXAMPLES

The present invention will hereinafter be described in further detail by the following Examples. It should however be borne in mind that the present invention is not limited at all by these Examples.

Example 1

Preparation of Extracts (1)

Green tea, oolong tea, washed and crushed ginger and washed and crushed green onion were separately extracted for 60 minutes in aliquots (10 times the weights of the respective materials) of hot water of 90° C., whereby respective extracts were prepared. They were separately concentrated in an evaporator, and extracts of [10% soluble solids (Brix 10°)] were obtained.

Example 2

Comparison of Proliferation Degrees of Lactic Acid Bacteria (1)

Using aliquots of a 20% skim milk powder solution as a basal medium, the ginger extract, green tea extract, oolong tea extract and green onion extract, which were obtained in Example 1, were added at 0.1% as lactic acid bacteria growth factors, respectively, and proliferation degrees of lactic acid bacteria were studied. Described specifically, the sterilized media were inoculated with 1% of a starter of *Lactobacillus casei* YIT9029, followed by cultivation at 37° C. for 48 hours. After the cultivation, the proliferation degrees of the lactic acid bacteria were compared by using as indices the acidities of the resulting cultures (titers determined by sampling 10-mL portions of the cultures and then titrating organic acids in the samples with 0.1 N caustic soda while using phenolphthalein as an indicator). The results are shown in Table 1. For the sake of comparison, "MEAST" (trademark for beer yeast autolysate; product of ASAHI BEER FOOD, LTD.) was added at 0.15%, and cultivation was conducted likewise. This amount of "MEAST" is practically the upper limit of added amount at which deleterious effect to the flavor of the cultured product is still permissible.

TABLE 1

| Lactic acid bacteria growth factor | Acidity |
|---|---|
| None | 9.5 |
| "MEAST" | 11.8 |
| Ginger extract | 12.8 |
| Green tea extract | 13.0 |
| Oolong tea extract | 13.1 |
| Green onion extract | 12.9 |

As is clear from Table 1, the growth promoting effects for the lactic acid bacteria by the addition of the ginger extract, green tea extract, oolong tea extract and green onion extract were more appreciable than that exhibited in the medium added with "MEAST".

Example 3

Comparison of the Proliferation Degree of the Lactic Acid Bacteria Among the Acidities of Extracting Solutions Using hot water (90° C.) and citric acid solutions (90° C.) of pH 3.0, 4.0 and 5.0, oolong tea extracts were prepared under the same conditions as in Example 1. They were separately concentrated in an evaporator, whereby extracts of [10% soluble solids (Brix 10°)] were obtained.

The individual extracts so obtained were added to aliquots of a 20% skim milk powder medium such that their concentrations became 0.1%. The resulting media were inoculated with *Lactobacillus casei* YIT9029, followed by cultivation at 37° C. for 48 hours. The acidities of the thus-obtained cultures were measured in the same manner as in Example 1. The results are shown in Table 2.

TABLE 2

| Extracting solvent | Acidity |
|---|---|
| Hot water | 13.7 |
| Citric acid solution (pH 3.0) | 17.2 |
| Citric acid solution (pH 4.0) | 17.1 |
| Citric acid solution (pH 5.0) | 15.5 |

As is shown in Table 2, the extracts obtained by conducting extraction with acid solutions of pH 5.0 and lower, especially pH 4.0 and lower exhibited marked growth promoting effect for the lactic acid bacteria.

Example 4

Preparation of Extracts (2)

Green tea, black tea, oolong tea, ginger and green onion were separately extracted in aliquots of a citric acid solution of pH 4.0. Under the same conditions as in Example 1, respective extracts were prepared. They were separately concentrated in an evaporator, and extracts of [10% soluble solids (Brix 10°)] were obtained.

Example 5

Comparison of Proliferation Degree Among Lactic Acid Bacteria (2)

Using aliquots of a 16% skim milk powder solution as a basal medium, the ginger extract, green tea extract, black tea extract, oolong tea extract and green onion extract, which were obtained in Example 4, were added at 0.1% as lactic acid bacteria growth factors, respectively. The sterilized media added with the respective extracts were inoculated with 1% of starters of various lactic acid bacteria shown in Table 3, followed by cultivation at 37° C. for 48 hours.

After the cultivation, the acidities of the resulting cultures were studied to determine the proliferation degrees of the lactic acid bacteria in a similar manner as in Example 2. For the sake of comparison, the basal media added at 0.15% with "MEAST" (trademark for beer yeast autolysate; product of ASAHI BEER FOOD, LTD.) was used. The results are shown in Table 3.

TABLE 3

| | Lactic acid bacteria growth factor | | | | | | |
|---|---|---|---|---|---|---|---|
| Tested cell strain | None | "MEAST" | Ginger extract | Green tea extract | Black tea extract | Oolong tea extract | Green onion extract |
| Lc. lactis YIT2013 | 7.3 | 7.8 | 8.2 | 8.5 | 8.0 | 7.9 | 8.3 |
| Lc. cremoris YIT2002 | 1.6 | 5.8 | 7.1 | 7.6 | 8.8 | 8.3 | 9.5 |
| St. thermophilus YIT2001 | 8.9 | 10.3 | 10.2 | 10.2 | 9.9 | 9.8 | 10.0 |
| L. bulgaricus YIT0098 | 17.5 | 20.3 | 19.0 | 18.1 | 19.2 | 19.5 | 17.8 |
| L. helveticus YIT0100 | 20.2 | 23.3 | 21.1 | 20.8 | 20.9 | 20.8 | 21.8 |
| L. jugulti YIT0085 | 10.1 | 15.3 | 13.8 | 14.0 | 13.5 | 13.0 | 12.0 |

TABLE 3-continued

| Tested cell strain | Lactic acid bacteria growth factor | | | | | | |
|---|---|---|---|---|---|---|---|
| | None | "MEAST" | Ginger extract | Green tea extract | Black tea extract | Oolong tea extract | Green onion extract |
| L. salivalius YIT0039 | 8.6 | 11.8 | 12.8 | 12.5 | 10.9 | 11.8 | 12.4 |
| L. fermentum YIT0031 | 2.4 | 8.5 | 7.2 | 7.2 | 6.9 | 7.0 | 6.8 |
| L. acidophilus YIT0070 | 10.6 | 13.5 | 13.8 | 14.1 | 14.6 | 15.0 | 14.2 |
| L. gasseri YIT0168 | 5.5 | 10.5 | 13.0 | 13.5 | 13.8 | 14.0 | 13.1 |
| L. gasseri YIT0192 | 3.3 | 10.0 | 10.2 | 10.9 | 11.2 | 11.8 | 10.7 |
| L. casei YIT0078 | 10.1 | 12.0 | 17.0 | 17.2 | 17.3 | 17.5 | 17.0 |
| L. casei YIT9029 | 9.5 | 11.8 | 16.5 | 16.7 | 16.9 | 17.1 | 16.6 |

(Note 1)
Lc.: Lactococcus, St.: Streptococcus, L.: Lactobacillus
(Note 2)
The values in the table indicate acidities.

As is clearly envisaged from Table 3, the growth promoting effect for lactic acid bacteria by the addition of these extracts were observed with respect to substantially all the tested cell strains as in the case of the addition of "MEAST" although it varied depending on the cell strains. Especially, the effect of the oolong tea extract was high. Further, its effect was more noticeable as the cell strain showed poorer growth in the basal medium. Even with lactic acid bacteria which do not grow well in animal milk media, cultures of high acidity and high viable count can be obtained in short time because the bacteria are allowed to actively grow owing to the growth promoting effect of these extracts. Further, these extracts brought about higher effect than "MEAST" when they were used in combination with Lactobacillus casei, Lactobacillus acidophilus, Lactobacillus gasseri, Lactococcus lactis subsp. Lactis, and Lactococcus lactis subsp. cremoris.

From a comparison among the tea extracts, the oolong tea extract was found to show superior growth promoting effect to any of the lactic acid bacteria to the other tea extracts, i.e., the green tea extract and the black tea extract.

Example 6

Comparison of Proliferation Degrees of the Lactic Acid Bacteria (3)

Using aliquots of a 16% skim milk powder solution, which contained 10% of glucose-fructose liquid sugar [10% soluble solids (Brix 70°)], as a basal medium, the same ginger extract, oolong tea extract and green onion extract as those employed in Example 4 were added at 0.5%, respectively, whereby test media were provided. After sterilization under heat, the respective media were inoculated with 0.5% of a starter of Lactobacillus casei YIT9029, followed by cultivation at 37° C. Variations in acidity were traced.

With respect to the individual test media, investigations were made for the numbers of cultivated days (the numbers of days required) needed to reach the same acidity as the ultimate acidity (28) in the cultivation in the basal medium alone (control) and also for the viable cell counts of the cultures when their acidities reached 28. The results are shown in Table 4.

TABLE 4

| Lactic acid bacteria growth factor | Number of days needed (days) | Viable cell count (cells/ml) |
|---|---|---|
| None | 6.5 | $3.5 \times 10^9$ |
| Ginger extract | 4.0 | $4.0 \times 10^9$ |

TABLE 4-continued

| Lactic acid bacteria growth factor | Number of days needed (days) | Viable cell count (cells/ml) |
|---|---|---|
| Oolong tea extract | 3.5 | $7.2 \times 10^9$ |
| Green onion extract | 3.8 | $5.2 \times 10^9$ |

As is apparent from Table 4, the growth of the bacteria was promoted by the addition of the extracts. Among the extracts, the effect of the oolong tea extract was high.

Example 7

Production and Organoleptic Evaluation of Fermented Milks

Aliquots (600-mL) of the respective cultures obtained in Example 6 were each added with glucose-fructose liquid sugar (400 mL) and sterilized water (1.5 L), and the resulting mixtures were homogenized, whereby fermented milks were produced. With respect to the four kinds of fermented milks of the lactic acid bacteria, a palate test was conducted by well-experienced 20 panellers. Through a three-point discrimination test, no difference was found to exist between the respective samples added with the extracts and the control.

Further, there was also an indication that the flavors of the extracts employed as growth factors for the lactic acid bacteria matched well with the flavor of the fermentation product of animal milk by the lactic acid bacteria. It was therefore confirmed that, when those extracts were used in cultivation for the production of fermented milks such fermented milks of lactic acid bacteria, the fermented milks were not deteriorated in flavor.

Example 8

Amount Dependency of the Effect of Water-Extracted Oolong Tea Extract on Flavor and Growth Promotion A 20% skim milk powder solution containing 10% of glucose-fructose liquid sugar [75% soluble solids (Brix 75°)] was used as a basal medium. To aliquots of the basal medium, the hot-water extracted oolong tea extract obtained in Example 3 and an oolong tea extract extracted with hot water of pH 4.0 were added in varied amounts. After sterilization under heat, the medium samples were each inoculated with 0.5% of lactic acid bacteria L. casei YIT9029, followed by cultivation at 37° C. until acidity of 30. Cultivation times and viable cell counts at the time where the acidty reached 30 were recorded. As a control, a culture obtained by conduction cultivation in the basal medium alone was used.

Next, 480-mL aliquots of the thus-obtained cultures were each added with glucose-fructose liquid sugar (400 mL) and sterilized water (1,620 mL), whereby 13 kinds of fermented milks of the lactic acid bacteria were produced. With respect to those fermented drinks, their flavors were examined by well-experienced 10 panellers. The results of the flavor examination are shown along with the cultivation times and viable cell counts in Table 5.

TABLE 5

| | Amount of added extract (%) | Cultivation time (hours) | Viable cell count (cells/ml) | Results of flavor examination |
|---|---|---|---|---|
| Extract extracted with hot water | 0.01 | 140 | $4.6 \times 10^9$ | Extremely good |
| | 0.05 | 133 | $5.3 \times 10^9$ | Extremely good |
| | 0.10 | 112 | $6.0 \times 10^9$ | Extremely good |
| | 0.50 | 102 | $6.3 \times 10^9$ | Good |
| | 1.00 | 89 | $6.7 \times 10^9$ | Slight tea flavor |
| | 2.00 | 85 | $7.1 \times 10^9$ | Puckery taste and tea flavor |
| Extract extracted with hot water of pH 4.0 | 0.01 | 130 | $5.5 \times 10^9$ | Extremely good |
| | 0.05 | 113 | $6.2 \times 10^9$ | Extremely good |
| | 0.10 | 95 | $7.0 \times 10^9$ | Extremely good |
| | 0.50 | 84 | $7.2 \times 10^9$ | Good |
| | 1.00 | 82 | $7.4 \times 10^9$ | Slight tea flavor |
| | 2.00 | 80 | $7.4 \times 10^9$ | Puckery taste and tea flavor |
| Control | — | 156 | $3.5 \times 10^9$ | Extremely good |

As is shown in Table 5, it was confirmed that the addition of 0.01% or more of any one of the extracts shortened the cultivation time and moreover increased the viable cell count. The extracts did not bring about any extra effect even when added in amounts greater than 0.5%. It was also confirmed that the flavor remained good up to 0.5% of any one of the extracts but the taste of each extract was felt when added in amounts of 1% and greater.

Example 9

Relationship Between the Amount of Free Oleic Acid in Low-Fat Yoghurt Medium and the Viable Cell Count at the Completion of Cultivation of Lactic Acid Bacteria A low-fat yoghurt medium was prepared with the composition of 20% skim milk powder (product of YOTSUBA MILK PRODUCTS CO., LTD.) and 3% glucose. Sodium oleate was added at rates of 0.003, 0.005, 0.01, 0.02 and 0.03 wt. % to aliquots of the medium, respectively, followed by sterilization at 100° C. for 60 minutes. The medium samples were inoculated with 0.5% of *Lactobacillus casei* YIT9029, followed by cultivation at 37° C. for about 200 hours. At the time of completion of the cultivation, the viable cell counts were measured. The viable cell counts (cfu/mL) were each obtained by spreading the corresponding culture, which had been diluted in 0.1% yeast extract as needed, onto a Rogosa agar plate with a spiral plater, incubating the agar plate at 37° C. for 3 days, and then counting the resultant colonies by a laser colony counter. The results are shown in FIG. 1. From FIG. 1, it has become evident that the count of viable cells upon completion of cultivation of *Lactobacillus casei* increases by the addition of oleic acid.

Example 10

Improving Effect on the Viability of Lactic Acid Bacteria in Stored Final Product by the Addition of Sodium Oleate To aliquots of the low-fat yoghurt medium of Example 9, sodium oleate was added at rates of 0.003, 0.005 and 0.01 wt. %, respectively. The medium samples were each inoculated with lactic acid bacteria, followed by cultivation to study effect of sodium oleate on the viability of the lactic acid bacteria. The cultivation was conducted at 37° C. until pH 3.6 to pH 3.8. Other conditions and the cell strain were the same as in Example 9.

On the side, 70% fructose-glucose liquid sugar was sterilized at 100° C. for 30 minutes, and the thus-obtained liquid sugar was provided as a syrup. The cultures and aliquots of the syrup, all of which had been obtained as described above, were mixed at a ratio of 1:1, and the resulting mixtures were filled in containers to obtain low-fat yoghurt products (the concentrations of oleic acid in the products were 15 μg/mL, 25 μg/mL and 50 μg/mL, respectively). Further, as a control, low-fat yoghurt not added with sodium oleate was produced.

Figure 2:
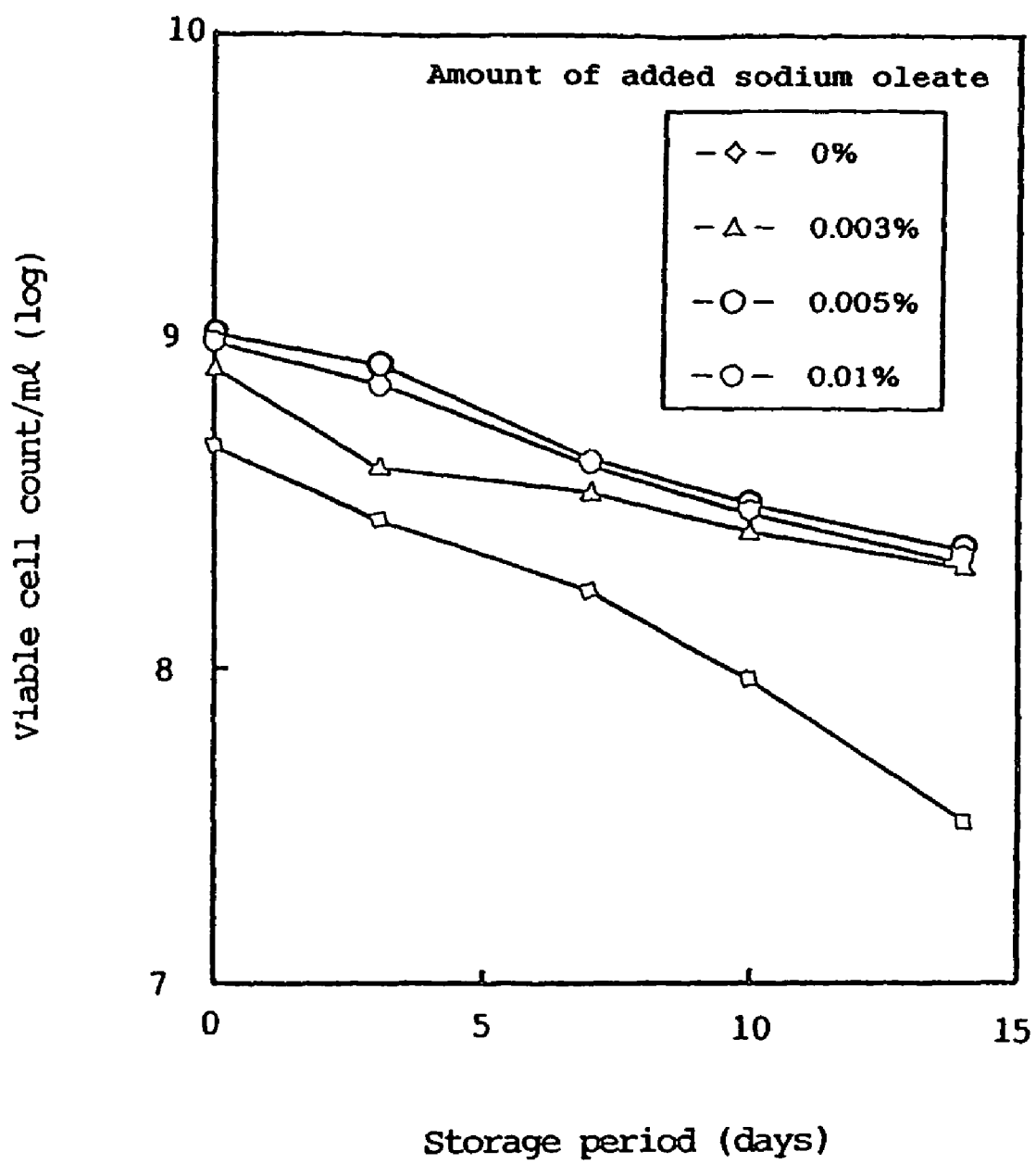
FIG. 2 is a plot of the relationship between number of stored days and viable cell count of the lactic acid bacteria.

The thus-obtained products were stored at 10° C. for 14 days. During the storage, the viable cell count of the respective products were investigated along the passage of time. The results are shown in FIG. 2. It has become clear from the results of FIG. 2 that high viability is retained even after 7-day storage by the addition of sodium oleate upon cultivation as opposed to the general tendency of a substantial decrease in viable cell count when the storage of a product exceeds 7 days (the variations in viable cell count on the 0th day of the storage of the products reflect the counts of viable cell in the cultures).

Example 11

To aliquots of the low-fat yoghurt medium of Example 9, oleic acid, sodium oleate and various emulsifiers, all of which are shown in Table 6, were added, respectively, such that their concentrations became 0.01% in terms of oleic acid content. Those medium samples were inoculated with 0.5% of *Lactobacillus casei* YIT9029, followed by cultivation to determine effects of these additives on the viable cell count of the lactic acid bacteria at the time of completion of the cultivation and also on the viability of the lactic acid bacteria. The culture was conducted at 37° C. until pH 3.6 to 3.8. Other conditions were set as in Example 9.

TABLE 6

| | Additive | Remarks |
|---|---|---|
| 1 | Oleic acid | |
| 2 | Sodium oleate | |
| 3 | Glyceryl oleate | Monoglyceride ≧ 90% |
| 4 | Pentaglyceryl monooleate | |
| 5 | Pentaglyceryl trioleate | |
| 6 | Hexaglyceryl monooleate | |
| 7 | Decaglyceryl decaoleate | |
| 8 | Sucrose oleate | Sucrose oleate ≧ 70% |
| 9 | Glyceryl oleate | Triglyceride |

After those cultures were stored at 5° C. for 5 days, they were mixed with aliquots of the syrup of Example 10 at a ratio of 1:1. The resulting mixtures were filled in containers to obtain low-fat yoghurt products. Further, as a control, low-fat yoghurt not added with oleic acid was produced.

The thus-obtained products were stored at 10° C. for 14 days. During the storage, the viable cell count of the respective products were investigated along the passage of time. The results are shown in Table 7.

TABLE 7

|  | Viable cell count (cfu/ml) | | | Viability on |
|---|---|---|---|---|
| Control | DAY 1 | DAY 7 | DAY 14 | Day 14 |
| 1 | $1.3 \times 10^9$ | $7.2 \times 10^8$ | $5.3 \times 10^8$ | 40.8% |
| 2 | $1.2 \times 10^9$ | $7.3 \times 10^8$ | $5.2 \times 10^8$ | 43.3% |
| 3 | $1.1 \times 10^9$ | $7.7 \times 10^8$ | $5.0 \times 10^8$ | 45.5% |
| 4 | $1.2 \times 10^9$ | $8.1 \times 10^8$ | $5.0 \times 10^8$ | 41.7% |
| 5 | $5.6 \times 10^8$ | $2.5 \times 10^8$ | $1.2 \times 10^8$ | 21.4% |
| 6 | $1.3 \times 10^9$ | $7.3 \times 10^8$ | $4.8 \times 10^8$ | 36.9% |
| 7 | $6.5 \times 10^8$ | $2.0 \times 10^8$ | $1.4 \times 10^8$ | 21.5% |
| 8 | $1.1 \times 10^9$ | $6.1 \times 10^9$ | $4.3 \times 10^8$ | 39.1% |

TABLE 7-continued

|  | Viable cell count (cfu/ml) | | | Viability on |
|---|---|---|---|---|
| Control | DAY 1 | DAY 7 | DAY 14 | Day 14 |
| 9 | $5.9 \times 10^8$ | $2.2 \times 10^8$ | $1.4 \times 10^8$ | 23.7% |
| Control | $3.2 \times 10^8$ | $1.6 \times 10^8$ | $2.6 \times 10^7$ | 8.1% |

It has been found from the results of Table 7 that low-fat yoghurt added with oleic acid shows a viability of 20% or higher even after stored at 10° C. for 2 weeks. It has also been found that use of oleic acid in the form of free oleic acid, an oleate salt or an oleate ester can provide an especially good viable cell count upon completion of cultivation and also particularly good viability.

Example 12

Effects of Individual Factors on the Maintenance of the Viable Cell Count of Lactic Acid Bacteria Aliquots (160 g) of skim milk powder, aliquots (30 g) of glucose and the ingredients indicated "+" in Table 8 were dissolved in aliquots of warm water to give total volumes of 1,000 mL, respectively [in the case of the ingredients indicated "+", were used 0.1% of the extract obtained in Example 4 as an oolong tea extract; 100 ppm, in terms of oleic acid, of monoglyceryl oleate as oleic acid; and 0.1% of "MEAST" (trademark for beer yeast autolysate; product of ASAHI BEER FOOD, LTD.) as a yeast extract]. Those medium samples were sterilized at 100° C. for 30 minutes and were then allowed to cool down to 37° C. They were inoculated with 0.1% of *Lactobacillus casei* YIT9029, followed by cultivation until pH 3.6. Fermented solutions of the lactic acid bacteria were hence obtained, respectively.

The fermented solutions were separately homogenized at 150 kg/cm², and were then mixed with aliquots (4,000 mL) of sterilized 13.8% sugar syrup. The resulting mixtures were filled in polystyrene contains and sealed, whereby fermented drinks of the lactic acid bacteria were obtained. After they were stored at 10° C. for 14 days, their viable cell count were measured. The results of this measurement are also shown in Table 8.

TABLE 8

|  | Sample 1 | Sample 2 | Sample 3 | Sample 4 | Sample 5 | Sample 6 | Sample 7 | Sample 8 |
|---|---|---|---|---|---|---|---|---|
| Oolong tea extract* | − | − | − | − | + | + | + | + |
| Oleic acid** | − | − | + | + | − | − | + | + |
| Yeast extract | − | + | − | + | − | + | − | + |
| Viable cell count per ml | $1.1 \times 10^8$ | $1.5 \times 10^8$ | $1.6 \times 10^8$ | $1.7 \times 10^8$ | $3.3 \times 10^8$ | $3.2 \times 10^8$ | $1.9 \times 10^{10}$ | $1.8 \times 10^9$ |
| Index | 8.04 | 8.20 | 8.95 | 9.11 | 9.23 | 9.26 | 9.20 | 9.26 |

*Oolong tea extract of Example 4
**Monoglyceryl oleate

From the results of Table 8, the orthogonal table shown in Table 9 was prepared in accordance with the method described on pages 292 to 300 in "Gendai Tokei Jitsumu Koza (Contemporary Statistics Practical Series) Text II" [published by Zaidan Hojin Jitsumu Kyoiku Kenkyusho (Practical Education Research Foundation)], and the percent contributions of the individual ingredients to the maintenance of the viable cell count of the lactic acid bacteria during storage were calculated. In Table 9, a represents the oolong tea extract, b oleic acid, and c the yeast extract; ab, ac and bc each indicate combined use of the corresponding two ingredients; and abc designates combined use of the three ingredients.

TABLE 9

|  | a | b | ab | c | ac | bc | abc |  |
|---|---|---|---|---|---|---|---|---|
| ① | 32.65 | 33.24 | 34.79 | 34.02 | 34.05 | 34.08 | 34.05 |  |
| ② | 35.59 | 35.00 | 33.45 | 34.22 | 34.19 | 34.16 | 34.19 |  |
| ① + ② | 68.24 | 68.24 | 68.24 | 68.24 | 68.24 | 68.24 | 68.24 |  |
| d = ② − ① | 2.94 | 1.76 | −1.34 | 0.20 | 0.14 | 0.08 | 0.14 |  |
| d/8 | 0.37 | 0.22 | −0.17 | 0.03 | 0.02 | 0.01 | 0.02 |  |
| d × d/8 | 1.08 | 0.39 | 0.22 | 0.01 | 0.00 | 0.00 | 0.00 | 1.70 |
| Contribution (%) | 63.45 | 22.74 | 13.18 | 0.29 | 0.14 | 0.05 | 0.00 |  |

It has been confirmed from Table 9 that oolong tea extract and monoglyceryl oleate both contribute to the maintenance of the viable cell count. It has also been found that the maintenance of the viable cell count can be synergistically enhanced when oolong tea and monoglyceryl oleate are used in combination.

The invention claimed is:
1. A fermented milk product made by:
providing an animal milk containing medium that has been supplemented with at least one oleic acid or a derivative of oleic acid and at least one acid-extracted ginger extract, acid-extracted green onion extract, or acid-extracted tea extract, said extracts having been extracted in a water-based solvent at pH 4 or below, and fermenting said animal milk medium with at least one lactic acid bacteria selected from the group consisting of *Lactobacillus casei, Lactobacillus acidolphilus, Lactobacillus gasseri, Lactococcus lactis* subsp, *lactis*, and *Lactococcus lactis* subsp, *cremoris* for a time and under conditions suitable for producing a fermented milk product;

wherein said at least one oleic acid or a derivative of oleic acid is selected from the group consisting of glyceryl oleate, polyglyceryl oleate, propylene glycol oleate, and sucrose oleate; and wherein said fermented milk comprises at least $1 \times 10^8$ cfu/mL of lactic acid bacteria and said lactic acid bacteria have a viability of at least 20% when said fermented milk is stored at 10° C. for 2 weeks.

2. The fermented milk product of claim 1, wherein said fermented milk product contains said oleic acid or derivative of oleic acid at a concentration ranging from 15 µg/mL to 60 µg/mL.

3. The fermented milk product of claim 1, wherein said fermented milk product contains said oleic acid or derivative of oleic acid at a concentration ranging from 15 µg/mL to 40 µg/mL.

4. The fermented milk product of claim 1
that contains 0.05 to 0.5% fat, and
which was prepared from an animal milk medium containing at least one of skim milk, liquid skim milk or skim milk powder.

5. The fermented milk product of claim 1, which was prepared by fermenting said animal milk medium with *Streptococcus thermophilus* bacteria.

6. The fermented milk product of claim 1, which was prepared by fermenting said animal milk medium with *Lactobacillus*.

7. The fermented milk product of claim 1, which was prepared by fermenting said animal milk medium with *Lactobacillus casei* bacteria.

8. The fermented milk product of claim 1, which was prepared by fermenting said animal milk medium with *Lactobacillus acidophilus* bacteria.

9. The fermented milk product of claim 1, which has been stored for 2 weeks at 10° C. and which contains at least $1 \times 10^8$ cfu/mL of lactic acid bacteria that have a viability of at least 20%.

10. The fermented milk product of claim 1, which has been produced from an animal milk medium containing said at least one acid-extracted ginger extract, acid-extracted green onion extract, or acid-extracted tea extract in an amount ranging from 0.02 wt. % to 2.0 wt. %.

11. The fermented milk product of claim 1 produced from an animal milk containing medium, which contains an acid-extracted ginger extract produced by extraction of ginger in a water-based or a water-alcohol-based solvent at a pH not higher than 4.0 at a temperature ranging from 60° C. to 120° C.

12. The fermented milk product of claim 1 produced from an animal milk containing medium, which contains acid-extracted green onion extract produced by extraction of Nebuka green onion or Ha green onion in a water-based or water-alcohol-based solvent at a pH not higher than 4.0 at a temperature ranging from 60° C. to 120° C.

13. The fermented milk product of claim 1 produced from an animal milk containing medium, which contains an acid-extracted tea extract produced by extraction of tea in a water-based or in a water-alcohol-based solvent at a pH not higher than 4.0 at a temperature ranging from 60° C. to 120° C.

14. The fermented milk product of claim 1, wherein the extract of tea, ginger or onion produced by extraction at pH 4 or below is supplemented into the animal milk medium without being removed from the water-based solvent.

15. The fermented milk product of claim 1, wherein the extract of tea, ginger or onion produced by extraction at pH 4 or below is supplemented into the animal milk medium after concentration by ultrafiltration or centrifugation.

16. The fermented milk product of claim 1, wherein the extract of tea, ginger or onion produced by extraction at pH 4 or below is supplemented into the animal milk medium in the form of a powdery extract produced by drying or lyophilizing the extract in the water-based solvent.

17. A method for fermenting an animal milk medium comprising:

supplementing an animal milk medium with oleic acid or a derivative of oleic acid and at least one acid-extracted ginger, acid-extracted green onion, or acid-extracted tea extract, said extracts having been extracted in a water-based solvent at pH 4 or below, and fermenting said animal milk medium with at least one lactic acid bacteria selected from the group consisting of *Lactobacillus casei, Lactobacillus acidolphilus, Lactobacillus gasseri, Lactococcus lactis* subsp, *lactis*, and *Lactococcus lactis* subsp, *cremoris*.

18. A method for fermenting an animal milk medium comprising:

fermenting said animal milk medium with at least one lactic acid bacteria selected from the group consisting of *Lactobacillus casei, Lactobacillus acidolphilus, Lactobacillus gasseri, Lactococcus lactis* subsp, *lactis*, and *Lactococcus lactis* subsp, *cremoris* to produce a fermented milk medium, and supplementing the fermented animal milk medium with oleic acid or a derivative of oleic acid to a concentration of 15 µg/mL to 60 µg/mL, and supplementing the fermented animal milk medium with at least one acid-extracted ginger, acid-extracted green onion, or acid-extracted tea extract said extracts having been extracted at pH 4 or below.

19. The method of claim 18, further comprising storing said supplemented fermented animal milk medium at 10° C. for 2 weeks, wherein at least 20% of the viable lactic acid bacteria at the time of formation of the fermented milk product remain viable after storage of the fermented milk product at 10° C. for 2 weeks.

20. A method for improving viability of lactic acid bacteria in a fermented milk product, which comprises:

adding an ingredient selected from oleic acid or a derivative thereof and at least one acid-extracted of ginger, acid-extracted green onion, or acid-extracted tea extract said extracts having been extracted in a water-based solvent at pH 4 or below, to an animal milk medium before or after fermentation by at least one lactic acid bacteria selected from the group consisting of *Lactobacillus casei, Lactobacillus acidolphilus, Lactobacillus gasseri, Lactococcus lactis* subsp, *lactis*, and *Lactococcus lactis* subsp, *cremoris*.

21. The method according to claim 20, wherein said oleic acid or derivative thereof is an oleate ester selected from the group consisting of glyceryl oleate, polyglyceryl oleate, sorbitan oleate, propylene glycol oleate, and sucrose oleate.

22. The method according to claim 20, wherein said oleic acid or derivative thereof amounts to at least 15 μg/mL in terms of oleic acid as a final concentration after conversion into a final product.

23. The method according to claim 20, wherein fat amounts to 0.05 to 0.5% of said fermented milk.

24. The method according to claim 20, further comprising storing said fermented milk at 10° C. for 2 weeks.

25. A fermented milk subjected to a viability improving method for lactic acid bacteria as defined in claim 20.

* * * * *